(12) United States Patent
Clarke

(10) Patent No.: US 8,046,057 B2
(45) Date of Patent: Oct. 25, 2011

(54) TISSUE STRUCTURE IDENTIFICATION IN ADVANCE OF INSTRUMENT

(76) Inventor: Dana S. Clarke, Tucson, AZ (US)

( * ) Notice: Subject to any disclaimer, the term of this patent is extended or adjusted under 35 U.S.C. 154(b) by 856 days.

(21) Appl. No.: 10/476,380

(22) PCT Filed: Apr. 11, 2002

(86) PCT No.: PCT/US02/11436
§ 371 (c)(1),
(2), (4) Date: Oct. 10, 2003

(87) PCT Pub. No.: WO02/083003
PCT Pub. Date: Oct. 24, 2002

(65) Prior Publication Data
US 2005/0027199 A1      Feb. 3, 2005

Related U.S. Application Data

(60) Provisional application No. 60/283,068, filed on Apr. 11, 2001.

(51) Int. Cl.
*A61B 5/00* (2006.01)
(52) U.S. Cl. .................. 600/478; 600/160; 600/129
(58) Field of Classification Search .......... 600/309–344, 600/473–480, 407, 408, 114, 104; 604/22, 604/164.01, 164.02
See application file for complete search history.

(56) References Cited

U.S. PATENT DOCUMENTS

| | | | | |
|---|---|---|---|---|
| 4,566,438 A | * | 1/1986 | Liese et al. | 600/176 |
| 5,280,788 A | * | 1/1994 | Janes et al. | 600/476 |
| 5,321,501 A | * | 6/1994 | Swanson et al. | 356/479 |
| 5,459,570 A | | 10/1995 | Swanson et al. | |
| 5,460,182 A | * | 10/1995 | Goodman et al. | 600/342 |
| 5,752,518 A | * | 5/1998 | McGee et al. | 600/424 |
| 6,004,314 A | | 12/1999 | Wei et al. | |

(Continued)

FOREIGN PATENT DOCUMENTS

GB      2 191 855 A      12/1987

OTHER PUBLICATIONS

Guiju Song et al., "Simultaneous measurements of the thickness and refractive index of microstructures in obscure specimen by optical coherence tomography," 111 Optik No. 12 (2000), pp. 541-543.

(Continued)

*Primary Examiner* — Sanjay Cattungal
(74) *Attorney, Agent, or Firm* — William A. Birdwell

(57) ABSTRACT

A method and apparatus for identifying tissue structures in advance of a mechanical medical instrument during a medical procedure. A mechanical tissue penetrating medical instrument (22) has a distal end for penetrating tissue in a penetrating direction. An optical wavefront analysis system (32-50) provides light to illuminate tissue ahead of the medical instrument and receives light returned by tissue ahead of the medical instrument. An optical fiber (30) is coupled at a proximal end to the wavefront analysis system and attached at a distal end to the medical instrument proximate the distal end of the medical instrument. The distal end of the fiber has an illumination pattern directed substantially in the penetrating direction for illuminating the tissue ahead of the medical instrument and receiving light returned therefrom. The wavefront analysis system provides information about the distance from the distal end of the medical instrument to tissue features ahead of the medical instrument.

16 Claims, 5 Drawing Sheets

U.S. PATENT DOCUMENTS

| | | | |
|---|---|---|---|
| 6,007,481 A * | 12/1999 | Riek et al. | 600/114 |
| 6,134,003 A | 10/2000 | Tearney et al. | |
| 6,157,856 A | 12/2000 | Sanghera et al. | |
| 6,175,669 B1 | 1/2001 | Colston et al. | |
| 6,178,346 B1 | 1/2001 | Amundsen et al. | |
| 6,193,676 B1 | 2/2001 | Winston et al. | |
| 6,196,226 B1 | 3/2001 | Hochman et al. | |
| 6,228,076 B1 | 5/2001 | Winston et al. | |
| 6,441,577 B2 * | 8/2002 | Blumenkranz et al. | 318/568.11 |
| 6,445,939 B1 * | 9/2002 | Swanson et al. | 600/342 |
| 6,485,413 B1 * | 11/2002 | Boppart et al. | 600/160 |
| 6,564,087 B1 * | 5/2003 | Pitris et al. | 600/478 |

OTHER PUBLICATIONS

Harold T. Yura, "Closed-form solution for the Wigner phase-space distribution function for diffuse reflection and small-angle scattering in a random medium," 17 J. Opt. Soc. Am. a, vol. 17, No. 12, Dec. 2000, pp. 2464-2474.

U.S. Appl. No. 60/283,068, filed Apr. 11, 2001, Clarke, Dana S.

* cited by examiner

TISSUE STRUCTURE IDENTIFICATION IN ADVANCE OF INSTRUMENT

RELATED APPLICATION

This application is based on provisional patent application No. 60/283,068, filed Apr. 11, 2001, and hereby incorporated by reference in its entirety.

FIELD OF THE INVENTION

This invention relates to medical procedures and apparatuses for performing medical procedures and, in particular, to methods and apparatuses for identifying tissues structures in advance of a tissue penetrating medical instrument.

BACKGROUND OF THE INVENTION

During invasive medical procedures employing a tissue penetrating medical instrument, such as a needle or a scalpel, there is a need to identify tissue structures in advance of the medical instrument so as to control the depth of penetration of the tip or cutting edge of the medical instrument. This may be done to ensure that the penetration is to the right depth, but usually more importantly, this is done to ensure that the medical instrument does not penetrate too deeply and thereby damage tissue structure unnecessarily.

During surgery important tissue is often damaged inadvertently. For example, biopsy patients often report a loss of sensation or motion control due to nerve damage sustained during surgery. It would be desirable to provide surgeons with a means to visualize better or measure the distance of the tip of a surgical device, such as a scalpel, to nerve tissue so that the surgeon can avoid penetrating tissue so deeply as to damage the nerve tissue.

Another current medical problem occurs during tests of certain body fluids or during localized injections, where a needle used to extract body fluids or inject medication must penetrate one body structure without penetrating a subsequent structure. For example, in performing a spinal tap it is desirable to penetrate the dural membrane containing the spinal fluid, but highly undesirable to penetrate, or even touch the spinal cord itself as that can cause sever injury and potentially permanent paralysis. Yet, this is generally carried out without the aid of any means for seeing the physical relationship of the tip of the spinal tap needle to the spinal structures or even a way of measuring the distance from the tip to structure that must not be penetrated. Similarly, in carotid injections in small laboratory animals it is often difficult to find the artery or vein in small animals, and it can be very difficult to keep from penetrating entirely through the artery or vein, once it is found. This can make drug delivery excessively time consuming and difficult to control.

The use of optical coherence domain reflectometry ("OCDR") has been disclosed as a technique for examining the reflectivity of an animal structure to a limited depth therein. In OCDR a short coherence length light source is used in a scanning Michelson interferometer to determine the distance of a point from which light is scattered to a reference position. This is disclosed, for example, in Swanson et al. U.S. Pat. No. 5,459,579 entitled METHOD AND APPARTUS FOR PERFORMING OPTICAL MEASUREMENTS, hereby incorporated by reference in its entirety. In particular, Swanson et al. discloses the use of a fiber optic Michelson interferometer having a test fiber placed adjacent to the surface of an animal structure and coupled through a lens for illuminating the structure and coupling the backscattered light back into the fiber. The backscattered light is then interfered with a scanning reference reflector to measure the reflectivity profile of the structure to a limited depth therein. However, the usefulness of this technique is limited by the size and vulnerability of the lens assembly associated with the test fiber.

Tearney, et al., U.S. Pat. No. 6,134,003, entitled METHOD AND APPARATUS FOR PERFORMING OPTICAL MEASUREMENTS USING A FIBER OPTIC IMAGING GUIDE WIRE, CATHETER OR ENDOSCOPE, hereby incorporated by reference in its entirety, extends OCDR to optical coherence tomography ("OCT"). Tearney et al. discloses that an OCDR test fiber may be combined with a catheter or endoscope having a scanning imaging system at the distal end thereof for obtaining multiple measurements of the distance to a body structure used to create a tomograhic image of the structure. Like Swanson et al., the disclosure of Tearney et al. is limited by the use of an optical system at the distal end of the test fiber, and it is static with respect to tissue depth. Colston et al. U.S. Pat. No. 6,175,669 entitled OPTICAL COHERENCE DOMAIN REFLECTOMETRY GUIDEWIRE, which discloses a fiber optic OCDR system for guiding a guidewire through an arterial system is similarly limited.

A method for analyzing tissue based on the information obtained from OCT is also discussed in Song et al., "Simultaneous measurements of thickness and refractive index of microstructures in obscure specimens by optical coherence tomography," Optik Volume 111, Issue 12, pages 541-543 (2000). Like Swanson et al. and Tearney et al., the disclosure of Song et al. is limited optics and essentially static depth measurements.

A technique for analyzing the contours of eye surfaces using OCT to provide autofocussing of a laser scalpel in eye surgery has been disclosed in Wei et al. U.S. Pat. No. 6,004,314 entitled OPTICAL COHERENCE TOMOGRAPHY ASSISTED SURGICAL APPARATUS. While in-line tomography, that is, obtaining OCDR data relative to various locations along the axis of propagation of the OCDR light is disclosed, this system is limited to use with a non physically invasive laser tool applied to the eye, which is especially adapted for light transmission, and is limited by the use of large, free-space optics for coupling the OCDR into the eye.

Winston et al. U.S. Pat. No. 6,228,076 entitled SYSTEM AND MTHOD FOR CONTROLLING TISSUE ABLATION describes the combining OCDR with an endoscope used for laser ablation to distinguish tissue. However, it is limited in applicability by the size of the endoscope and distal optics.

In both manual and robotic surgery, the surgeon and surgical robot must know: (a) where a cut is occurring, and (b) what is being cut. This information describes the current state of a procedure. In addition, ideally the surgeon and robot would know where a cut is about to occur and what is about to be cut. This information, referred to as feedforward, is much harder information to acquire.

A surgical robotic arm typically provides, from sensors mounted thereon, six position values, six velocity values, and six acceleration values. Combining this information with basic anatomy information can let the robot know where and what it is cutting and to estimate what it is cutting, but does not allow the robot actually to sense the tissue that is being cut or to sense ahead of the cut. Such advance, or feedforward, information, as well as feedback, has been supplied for surgical procedures by, magnetic resonance imaging ("MRI") and ultrasound on a routine basis. However, neither of these techniques has sub-millimeter resolution. So, for delicate work they are not optimal. In addition, MRI is severely constrained in application by its size, its cost, and the strength of the magnets involved. Ultrasound has considerably worse spatial resolution than MRI.

Accordingly, there is a need for a method and system that can be used both to determine the current state of a mechanical tissue penetrating medical instrument, such as a mechanical scalpel, biopsy needle, or injection needle, to scan tissue ahead of the medical instrument while it is moving, to identify and avoid damaging tissue structures such as blood vessels and nerves.

SUMMARY OF THE INVENTION

The aforementioned need is met by the present invention, which provides a method and apparatus for identifying tissue structures in advance of a mechanical medical instrument during a medical procedure. A mechanical tissue penetrating medical instrument has a distal end for penetrating tissue in a penetrating direction. An optical wavefront analysis system provides light to illuminate tissue ahead of the medical instrument and receives light returned by tissue ahead of the medical instrument. An optical fiber is coupled at a proximal end to the wavefront analysis system and attached at a distal end to the medical instrument proximate the distal end of the medical instrument. The distal end of the fiber has an illumination pattern directed substantially in the penetrating direction for illuminating the tissue ahead of the medical instrument and receiving light returned therefrom. The wavefront analysis system provides information about the distance from the distal end of the medical instrument to tissue features ahead of the medical instrument.

In one embodiment, the medical instrument is a needle for extracting body fluid or injecting medication. The optical fiber is embedded in the needle longitudinally thereof. Multiple fibers may be used to provide improved information content. In another embodiment one or more optical fibers are embedded in a scalpel. Preferably, the wavefront analysis system is an OCDR system, but other means for analyzing the wavefront information could be used.

The foregoing and other objects, features, and advantages of the invention will be more readily understood upon consideration of the following detailed description of the invention, taken in conjunction with the accompanying drawings.

DETAILED DESCRIPTION OF THE INVENTION

The method and apparatus of the present invention uses optical fibers aligned along a needle, scalpel or other mechanical cutting tool to both transmit and receive optical information directly in front of the cutting surface. OCDR is used to determine the depth of boundaries immediately in advance of a cutting surface such as a needle tip or scalpel blade. This information can be used to alert either a medical professional or a surgical robot to the presence of an upcoming boundary and possibly identify the tissue.

Figure 1A:
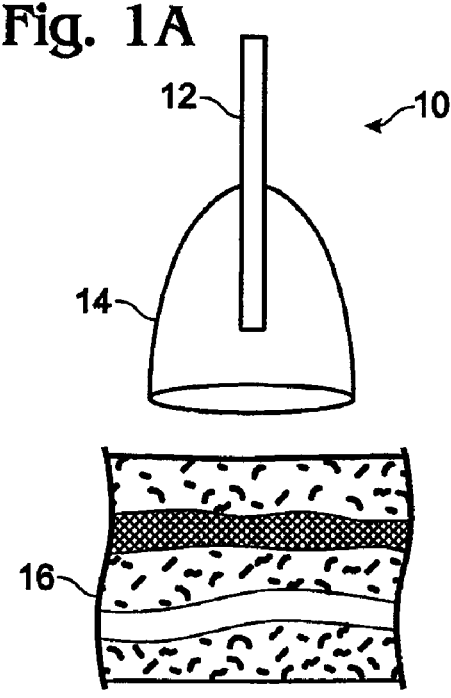
FIG. 1(a) is an illustration of a test fiber and associated lens adjacent tissue in a fiber optic Michelson interferometer OCT system for surface scanning according to the prior art.
Figure 1B:
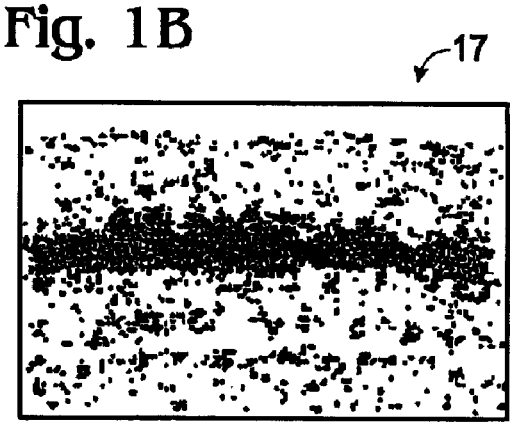
FIG. 1(b) is an illustration of a two-dimensional slice of an OCT image produced by the prior art system of FIG. 1(a).

The basic concept of prior art OCT 10 is illustrated by FIGS. 1(a) and 1(b), which shows a typical test fiber 12 and associated distal optic 14 in relation to a tissue sample 16 to be scanned. This prior art system, which does not mechanically penetrate the tissue, can produce a two-dimensional tomographic image 17 of relatively limited depth of, for example, 1-2 millimeters.

Figure 2A:
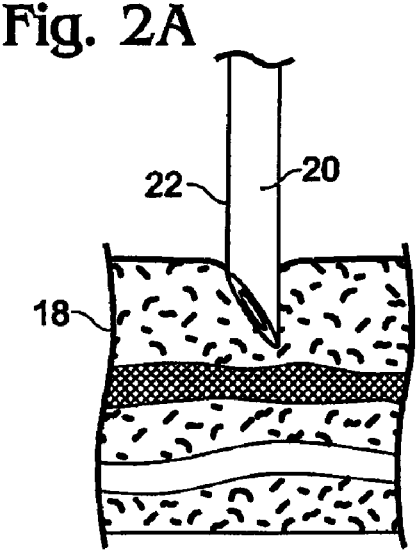
FIG. 2(a) is an illustration of a test fiber adjacent tissue in a fiber optic Michelson interferometer OCDR system for axial scanning according to the present invention.
Figure 2B:
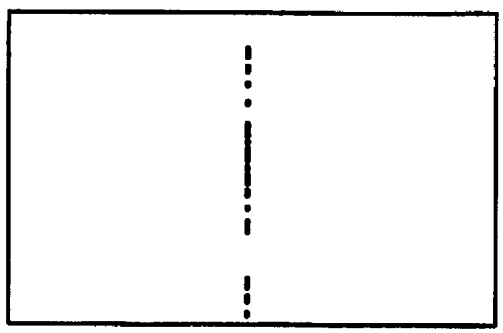
FIG. 2(b) is an illustration of a one-dimensional slice of an OCDR image produced by the method and apparatus of the present invention.

In contrast, the apparatus for identifying tissue structures ahead of a mechanical tissue penetrating instrument 18 according to the present invention, employs an axial, dynamic OCDR system, as shown in FIGS. 2(a) and 2(b). In this case, a fiber 20 is imbedded in a mechanical tissue penetrating medical instrument such as needle 22, and the tissue 24 is scanned in the axial direction of movement of the instrument as it penetrates the tissue. This produces a one-dimensional axial scan 26, as shown in FIG. 2(b). Since the fiber is embedded in the instrument, only the fiber core is actually required, the instrument itself providing the mechanical protection for the core. No optic is required to be associated with the end of the fiber, as it has been found surprisingly that, in this application, backscattered light captured by the fiber end face is sufficient to provide the desired one-dimensional image. Because a single mode fiber has such a small diameter, on the order of 12.5 micrometers (micron), it can be carried into the tissue by the mechanical instrument, thereby probing the depth of the tissue ahead of the instrument as it is advanced.

Figure 3:
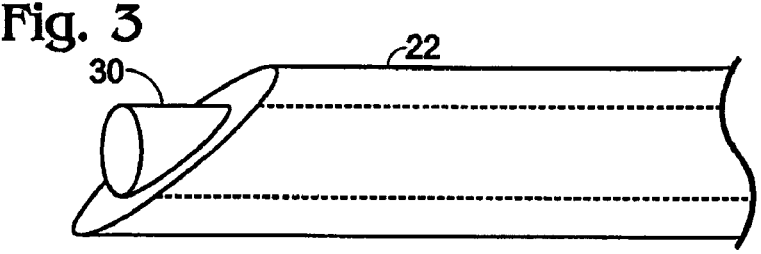
FIG. 3 is an exemplary needle for use in a tissue boundary identification method and apparatus in accordance with the present invention.

Turning to FIG. 3, a typical instrument with which the present invention is to be used is a cored needle 28, such as the type of needle that is used to inject a spinal block in a surgical patient. Such a needle is typically about one millimeter in diameter. As shown, the core is filled with a single mode fiber 30, surrounded by cladding, when the needle is inserted into an animal subject. While the needle penetrates deeper and deeper into the tissue, the light emitted from the core propagates ahead and some is scattered back into the end face of the fiber. As the needle is advanced, the fiber "sees ahead" of the needle 1-2 millimeters, which is enough to stop the needle before a critical boundary is penetrated.

Figure 4:
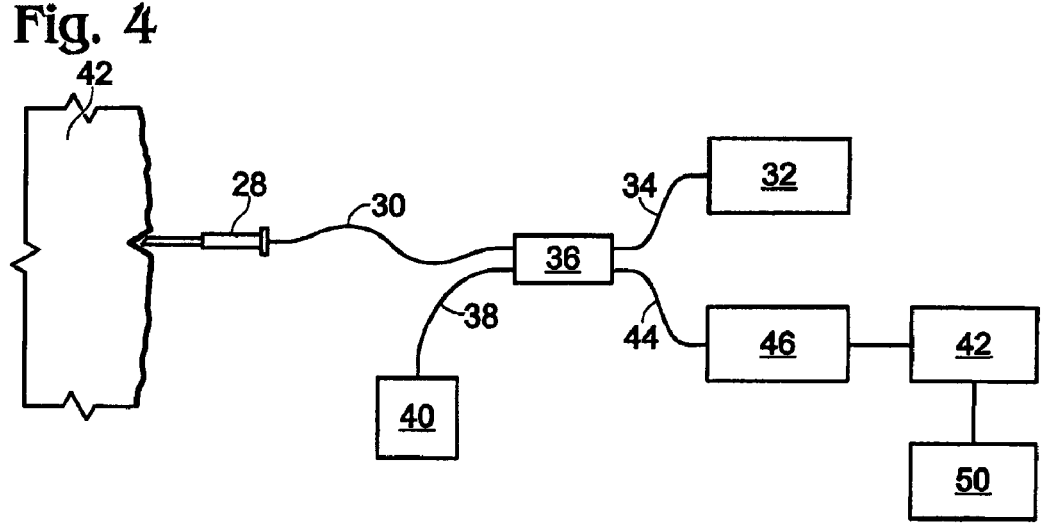
FIG. 4 is a block diagram of an OCDR analysis system for use with a tissue penetrating medical instrument in accordance with the present invention.

FIG. 4 shows a block diagram of a typical OCDR system suitable for use in the present invention. OCDR is a distance-measuring tool that relies on the fact that if a sufficiently broad band source is used in an interferometric system, interference fringes can only be generated when the two optical path lengths are equal. The depth resolution of the interferometer is directly proportional to the bandwidth of the source through $$\Delta(nl) \propto \frac{1}{c\Delta v}.$$

The optical path length to the sample can be measured through knowledge of the position of the reference mirror, which is obtained by other means.

There are several ways of scanning the position of the reference mirror. By way of example, the first method involves scanning the reference mirror with a predetermined position and velocity profile. This method is simple to implement but requires compensation for the doppler shift of the moving reference mirror. Alternatively, a series of fixed reflectors at different lengths can be scanned by a rotating prism or mirror. Although it is more complex to implement, doppler compensation is not required and allowable scan rates are much higher.

In FIG. 4, the needle 28 carries the test fiber 30 into the tissue that is penetrated. Light generated by a low-coherence source 32 is coupled through a source fiber 34 and fiber coupler 36 both to the test fiber 28 and a reference fiber 38. The reference fiber illuminates a scanning reference reflector 40, which reflects light back into the reference fiber. Light reflected back from tissue 42 along the test fiber and from the reference 40 along the reference fiber is couple to a detector fiber 44 and produces interference at the detector 46. The analog output of the detector is processed by signal processor 48, whose output is analyzed by computer 50 to display an axial tomographic image of the tissue in front of the needle as the needle progresses through the tissue.

Figure 5:
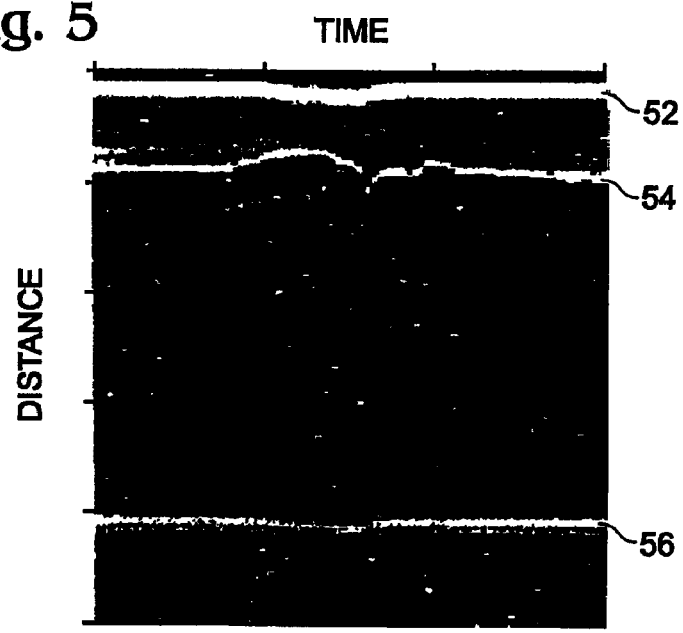
FIG. 5 is a picture of the tissue structure of the spinal sheath, synovial fluid and cord of a pig along the axis of advancement and ahead of a stationary penetrating medical instrument, produced in accordance with the present invention.
Figure 6:
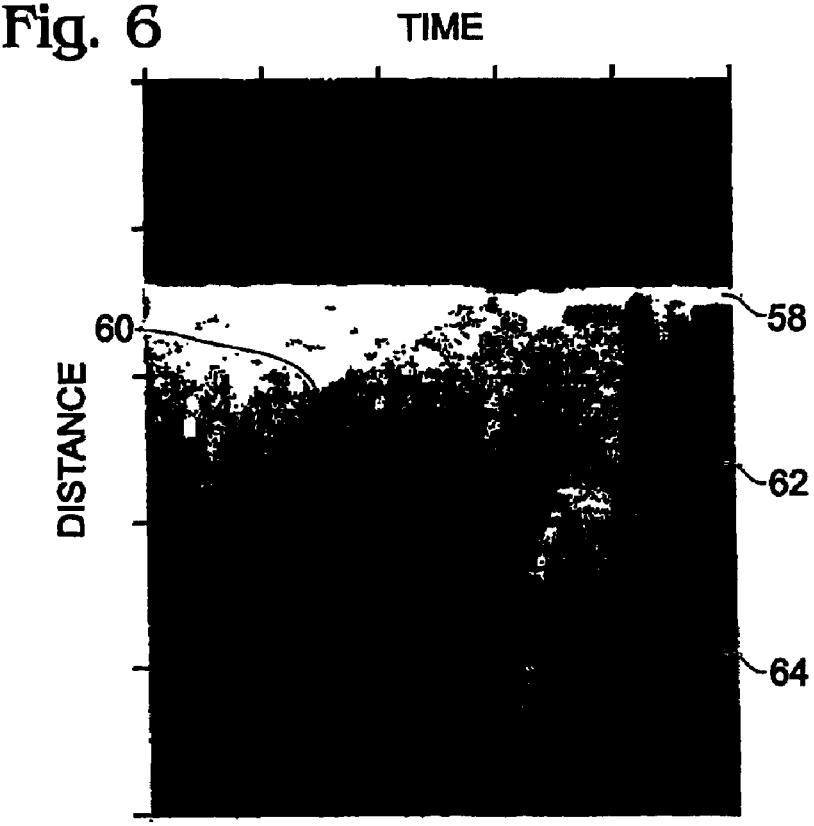
FIG. 6 is a picture of the tissue structure of the abdomen of a mouse along the axis of advancement and ahead of a penetrating medical instrument moving at a substantially steady rate, produced in accordance with the present invention.

The operation of the present invention is shown by FIGS. 5 and 6, which are pictures of actual data produced by the invention. In FIG. 5, the needle 28 has been placed on the surface of the spinal cord of an ex vivo laboratory pig and held stationary. In the picture of FIG. 5, the vertical axis represents, downwardly, the distance into the spinal from the end of the penetrating medical instrument. The horizontal axis represents time. Item 52 is a reflection off the distal face of the test fiber 30, item 54 is the spinal cord dural, and item 56 is the boundary of the spinal nerves. Since the needle has been held stationary, the reflections are substantially linear, the variations coming from random movements. In FIG. 6, the needle 28 has been inserted into the abdomen of an ex vivo laboratory mouse and advanced forward at a substantially constant rate so as to penetrate the structures therein. Item 58 is the reflection of the distal face of the test fiber. Item 60 is the boundary of the stomach. Item 62 is the boundary of the liver. It can be seen that as time (depth of penetration) progresses, the boundary reflections move closer in the picture to the fiber face reflection. (Item 64 is an artifact caused by rapid puncture through the liver.)

Figure 7A:
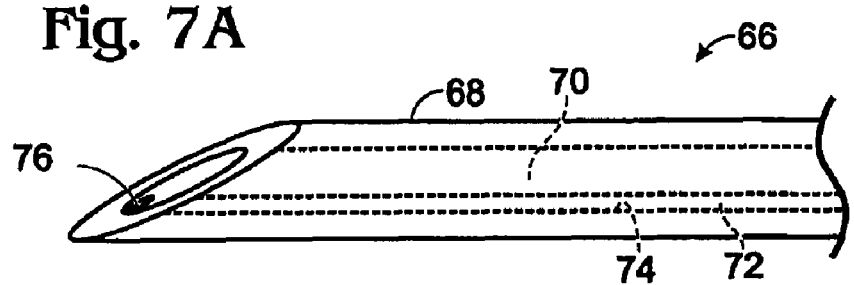
FIG. 7(a) shows a first embodiment of a spinal block needle equipped with a fiber in accordance with the present invention.
Figure 7B:
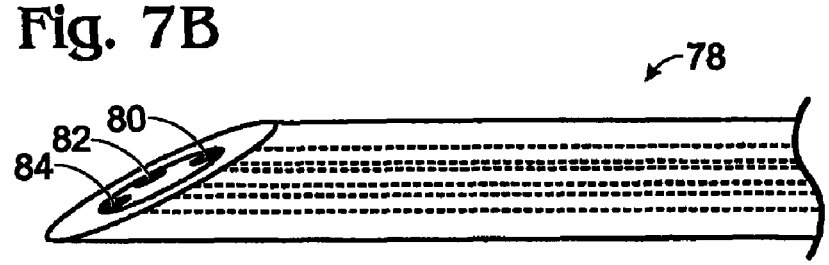
FIG. 7(b) shows a second embodiment of a spinal block needle equipped with a fiber in accordance with the present invention.
Figure 7C:
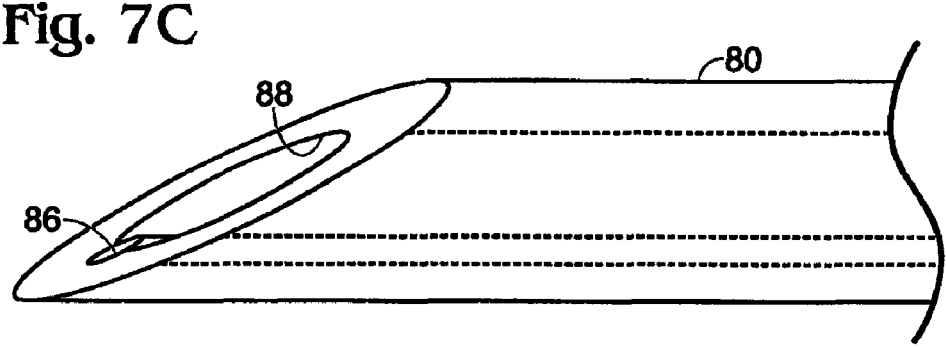
FIG. 7(c) shows a third embodiment of a spinal block needle equipped with a fiber in accordance with the present invention.

Alternative embodiments of spinal block needles according to the present invention are shown in FIGS. 7(a), 7(b) and 7(c). In FIG. 7(a), the needle 66 has an outer sheath 68 and a removable inner core 70. The needle is inserted into and penetrates the tissue close to the spinal cord for injecting anesthetic. A test fiber 72 is embedded in a groove 74 in the core 70, the distal end of 76 of the fiber being disposed proximate the distal end of the sheath 68. The test fiber is used in accordance with the present invention to guide the needle close to the spinal cord without penetrating it. The inner core 70 is then removed, along with the fiber, and the anesthetic is injected.

In FIG. 7(b), a needle 78 is like needle 66, except that it is equipped with several test fibers 80, 82 and 84 coupled alternately to the OCDR system. This enables the measurements to be averaged to reduce measurement errors.

In FIG. 7(c), a needle 80 is like the needle 66 of FIG. 7(a), except that a test fiber 86 is embedded in a groove in the inner wall 88 of the needle. The needle may or may not be equipped with a core.

In all of FIGS. 7(a)-(c) it is to be recognized that the fiber could be replaced with a waveguide other than a fiber, for example a semiconductor deposited into a groove etched into a wall of the needle, or a metal microtube. Such an alternative waveguide is preferably coupled at its proximal end to a fiber for connection to the OCDR system.

Figure 8:
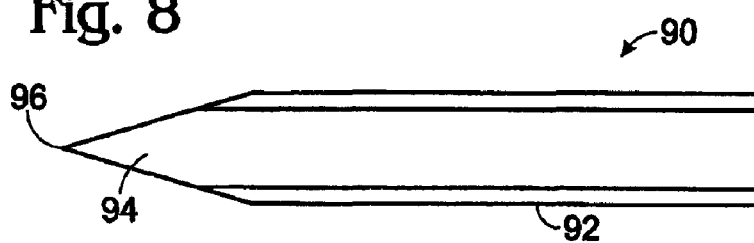
FIG. 8 shows a tissue-penetrating device equipped with a fiber tip in accordance with the present invention.

FIG. 8 illustrates either a needle or a scalpel where the tip of the glass fiber is itself a cutting tool. Thus, the mechanical tissue penetrating instrument 90 comprises an outer rigid wall 92, which could be either tubular (in the case of a needle) or flat (in the case of a scalpel, and an inner fiber core 94 which terminates in a tip 96. The tip is a sharp edge that not only provides narrow beam forward illumination, but acts as the cutting edge for the instrument. This device is particularly adapted for use in cosmetic surgery, where very fine, sharp cutting edges are needed. Since breakage of the edge can be immediately detected by the OCDR system the use of such a glass cutting tool is enabled with minimum risk that a broken edge will cause patient damage.

Figure 9:
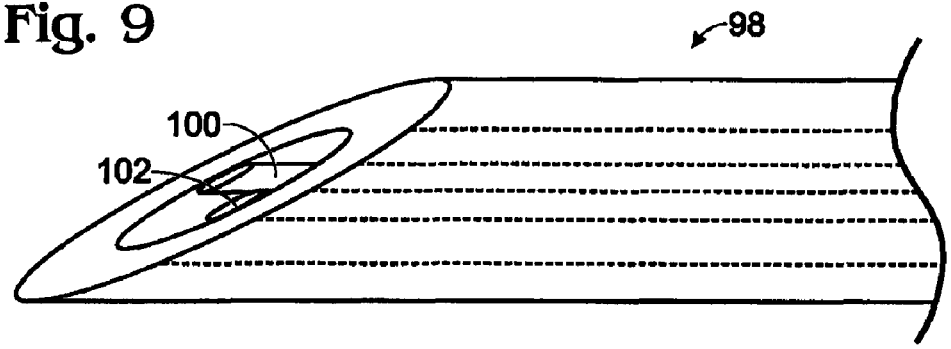
FIG. 9 shows a side view of a tissue-penetrating needle equipped with a transmitting fiber and a receiving fiber in accordance with an alternative embodiment of the present invention.
Figure 10:
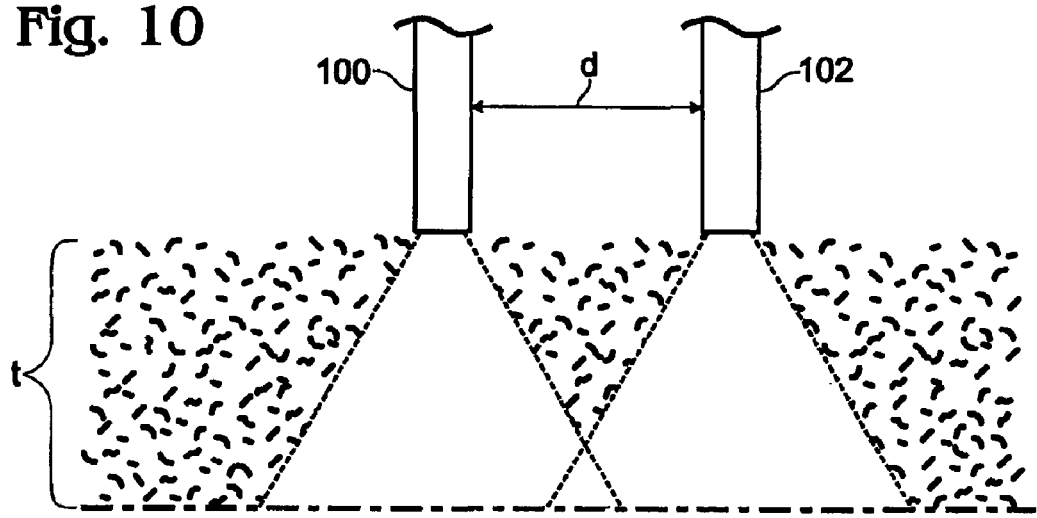
FIG. 10 is an illustration of the use of a transmitting fiber and a receiving fiber as shown in FIG. 9 in relation to tissue, in accordance with the present invention.
Figure 11:
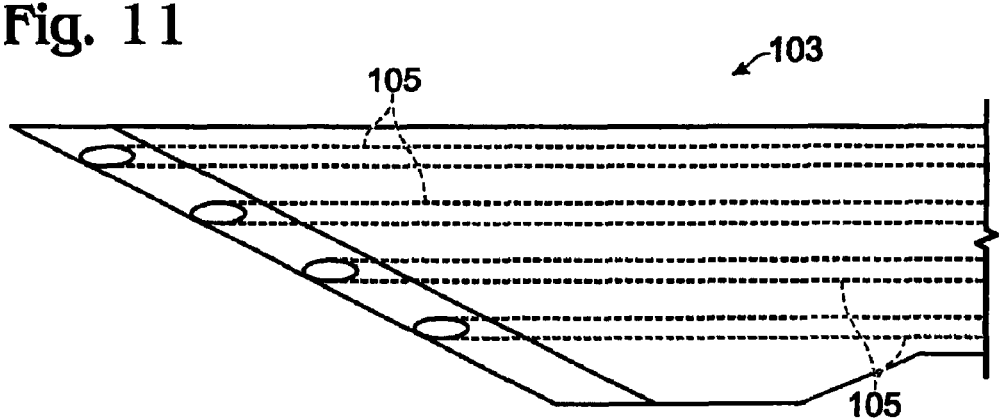
FIG. 11 shows a scalpel equipped with a plurality of fibers in accordance with the present invention.

As indicated above, a needle or other mechanical tissue-penetrating instrument may be equipped with two fibers. Thus, in FIG. 9, a needle 98 is equipped with fibers 100 and 102. FIG. 10 shows the respective fields of view of fibers 100 and 102. Similarly, FIG. 11 shows a scalpel 103 equipped with a plurality of fibers 105. The return from such multiple fibers can be used in several ways: (a) to average the inputs as a means of speckle reduction; (b) to increase the light collection efficiency of the system; and (c) to aid in tissue discrimination.

The distance light travels from a fiber to a boundary and directly back to the fiber face—neglecting scattering—is: $OPD_1=2$ nt. The distance light travels from one fiber, to a boundary and back to the other fiber is:

$$OPD_2 = 2n\sqrt{\frac{d^2}{4} + t^2}$$

The difference is:

$$OPD_2 - OPD_1 = 2n\left(\sqrt{\frac{d^2}{4} + t^2} - t\right)$$

For small motion along z we can get:

$$\Delta(OPD_2 - OPD_1) = 2n\left(\sqrt{\frac{d^2}{4} + (\Delta z)^2} - \Delta z\right)$$

Assuming the motion is small enough not to alter the location of the boundary in question, the only unknown in the above equation is the index of refraction of the intervening medium, which can be computed. In addition, the width of overlap cones of the respective fibers is a function of the scattering strength of the medium, as is the direct return signal as well.

Figure 12:
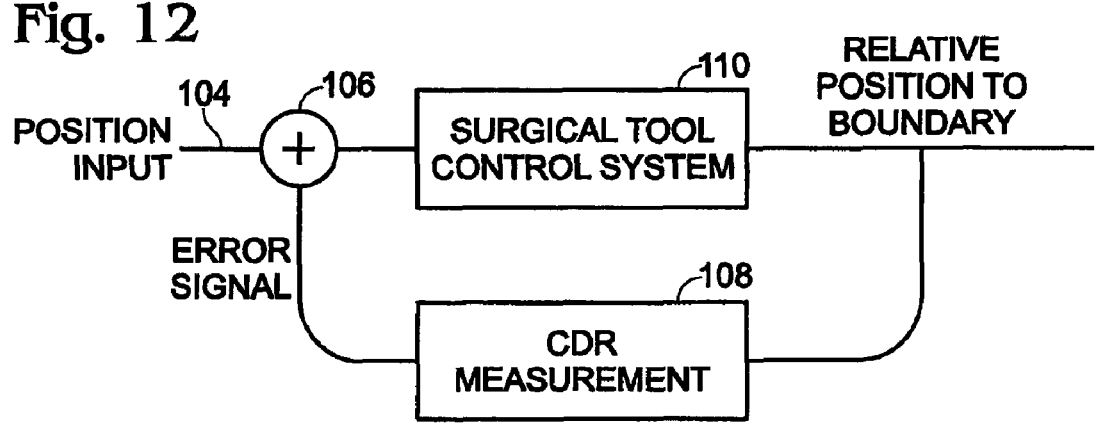
FIG. 12 shows a flow chart of a representative control system using feed back to guide a mechanical tissue penetrating medical instrument according to the present invention.

The present invention can be used as part of a control system for automatic or quasi-automatic robotic surgery. This is illustrated by FIG. 12. A position input is provided by a physician at 104. an adder 106 receives an error signal from the OCDR system 108 and produces a sum signal to a surgical too control system 110.

To appreciate the control capability offered by the invention, it is useful to think of the information that it provides in terms of a state vector, each element of the vector describing a state or condition of a surgical system. For example, in a robotic needle probe, an ideal state vector would include elements representing at least the following parameters: needle position, $\vec{r}$; angular position, $\vec{\phi}$; needle velocity, $\dot{\vec{r}}$; needle angular velocity, $\dot{\vec{\phi}}$; needle acceleration, $\ddot{\vec{r}}$; needle angular acceleration, $\ddot{\vec{\phi}}$; tissue type at tip location; tissue type 0.25 mm beyond tip location; issue type 0.50 mm beyond tip location; tissue type as far in front of the cutting edge of the instrument as it is possible to measure. In the event that it is impossible to identify the exact tissue type, it is still useful to identify the location of a change in tissue type. Knowledge of the position vector $\vec{r}$ of the cutting edge, and the anatomy of the subject could be used to make a useful estimate of the location and type of a tissue boundary.

The present invention can be used to augment a conventional state vector to provide feedforward, as well as feedback, information as described above. This can be used either to provide valuable information to a surgeon through an appropriate interface, or in the control algorithm for a surgical robot.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. An integrated medical needle and optical system for identifying tissue structures in advance of said needle during a medical procedure, comprising:
   a medical needle having a distal end for piercing tissue in a penetrating direction ahead of said distal end, said needle having an exterior surface;
   an optical wavefront analysis system for providing light to illuminate tissue ahead of said needle, receiving light returned by tissue ahead of said needle and providing information about the distance from said distal end of said needle to tissue features ahead of said needle; and
   at least one single optical fiber disposed within the interior of said needle, coupled at a proximal end to said wavefront analysis system, and having a distal end disposed proximate said distal end of said needle, said distal end of said one single optical fiber having an illumination pattern directed substantially in said penetrating direction for illuminating the tissue ahead of said needle and receiving light returned therefrom without the assistance of a separate optical element coupled to said one single fiber at the distal end thereof.

2. The integrated needle and optical system of claim 1, wherein said wavefront analysis system comprises a coherent domain reflectometer.

3. The integrated needle and optical system of claim 1, wherein said needle has an interior channel formed therein along the longitudinal axis thereof and said one single fiber is disposed in said channel.

4. The integrated needle and optical system of claim 1, further comprising at least one additional single optical fiber disposed within said needle along the longitudinal axis of said needle and terminating with its distal end proximate the tip of the needle, said at least one additional single fiber being coupled at a proximal end to a wavefront analysis system.

5. The integrated needle and optical system of claim 1, wherein said needle further comprises a cutting edge, said distal end of said one single fiber being at least a part of said cutting edge.

6. The integrated needle and optical system of claim 1, further comprising a robotic surgery apparatus for positioning said needle and said wavefront analysis system provides a feedback signal to said robotic surgery apparatus for controlling the position of said needle.

7. The integrated needle and optical system of claim 1, wherein said wavefront analysis system is adopted to identify, from said light returned to the distal end of said one single fiber, the distance from said distal end of said needle to a critical boundary within said tissue.

8. The integrated needle and optical system of claim 1, wherein said fiber consists essentially of a single-mode fiber core embedded in said needle.

9. The integrated needle and optical system of claim 1, wherein said needle comprises a spinal block needle having a proximal end, a distal end, and an aperture extending there through from said proximal end to said distal end, said needle further having a removable core for insertion within said needle and having a distal end disposed at said distal end of said needle when said core is inserted within said needle, said optical fiber being embedded within said core, said distal end of said one single fiber being disposed substantially at said distal end of said core.

10. The integrated needle and optical system of claim 9, wherein said wavefront analysis system is adapted to identify, from said light scattered into said distal end of said one single fiber, the distance from said distal end of said needle to a critical boundary within said tissue.

11. The integrated needle and optical system of claim 9, wherein said one single optical fiber is embedded in a groove in said core.

12. A method for identifying tissue features in advance of a tissue penetrating needle during a medical procedure, comprising:
- coupling light into a proximal end of at least one single optical fiber disposed within the interior of a tissue penetrating needle having a distal end for piercing tissue in a penetrating direction of said distal end so as to cause the light to be emitted from a distal end of said one single fiber disposed proximate said distal end of said needle into tissue with an illumination pattern substantially in said penetrating direction in advance of said needle;
- coupling from said proximal end of said one single fiber to a wavefront analysis system light that is emitted from said distal end of said one single fiber and returned thereto without the assistance of a separate optical element coupled to said one single fiber at the distal end thereof; and
- while said needle is advanced into tissue, analyzing said light returned from the tissue to determine the distance from said distal end of the needle to tissue features in advance of the needle.

13. The method of claim 12, wherein said analyzing light employs optical coherent domain reflectometry.

14. The method of claim 12, wherein said illumination pattern is achieved without the aid of an imaging optical element separate from said one single fiber.

15. The method of claim 12, further comprising
- coupling light into a proximal end of a second single optical fiber disposed within the interior of said mechanical tissue penetrating needle so as to cause the light to be emitted from a distal end of said second single fiber disposed proximate said distal end of said needle into said tissue substantially in said penetrating direction in advance of said needle;
- coupling from said proximal end of said second single fiber to said wavefront analysis system light that is emitted from said distal end of said second single fiber and returned thereto;
- while the needle is advanced into tissue, analyzing said light returned from the tissue to the said second single fiber to determine the distance from said distal end of the needle to tissue features in advance of the needle; and
- averaging the distances determined using both single fibers.

16. A tissue penetrating needle for identifying tissue in advance thereof, comprising:
- a tissue penetrating needle having a distal end for piercing tissue in a penetrating direction ahead of said distal end and a surface defining the exterior of said needle;
- at least one single optical fiber, having a proximal end and a distal end, said one single fiber being contained within the interior of said needle so that said distal end of said one single fiber is adjacent said distal end of said needle and said one single fiber extends along said needle toward said proximal end of said needle, said proximal end of said fiber having a mechanism for coupling said one single fiber to an optical sensing system, and said distal end of said fiber being positioned so as to direct and receive light along said penetrating direction without the assistance of a separate optical element coupled to said one single fiber at the distal end thereof.

* * * * *